United States Patent [19]

Pinchuk et al.

[11] Patent Number: 4,946,466
[45] Date of Patent: Aug. 7, 1990

[54] TRANSLUMINAL ANGIOPLASTY APPARATUS

[75] Inventors: Leonard Pinchuk; John B. Martin, both of Miami, Fla.

[73] Assignee: Cordis Corporation, Miami, Fla.

[21] Appl. No.: 318,620

[22] Filed: Mar. 3, 1989

[51] Int. Cl.$^5$ .............................................. A61M 29/02
[52] U.S. Cl. ........................................ 606/194; 604/96; 604/95
[58] Field of Search ..................... 128/325, 344, 348.1; 604/96–103

[56] References Cited

U.S. PATENT DOCUMENTS

| | | | |
|---|---|---|---|
| 4,456,000 | 6/1984 | Schjeldahl et al. | 604/96 X |
| 4,490,421 | 12/1984 | Lavy | 128/344 |
| 4,793,350 | 12/1988 | Mar et al. | 128/344 |
| 4,838,268 | 6/1989 | Keith et al. | 128/344 |
| 4,846,174 | 7/1989 | Willard et al. | 128/344 |
| 4,848,344 | 7/1989 | Sos et al. | 128/344 |

FOREIGN PATENT DOCUMENTS 624639 9/1978 U.S.S.R. ............................ 128/3341

Primary Examiner—C. Fred Rosenbaum
Assistant Examiner—Corinne Maglione
Attorney, Agent, or Firm—Lockwood, Alex, FitzGibbon & Cummings

[57] ABSTRACT

An apparatus for performing transluminal angioplasty is provided. The apparatus of the present invention may be utilized in blood vessels of very small cross-sectional diameter as well as in blood vessels of larger diameter. The apparatus of the present invention includes a hollow metallic guidewire with an expandable balloon member affixed to the hollow guidewire at or near the distal end thereof. The hollow guidewire is preferably metallic and more preferably made of stainless steel. In the preferred embodiment, the metallic guidewire provides a catheter of extremely small diameter while simultaneously imparting good torque control and excellent pushability of the apparatus within the blood vessel being treated.

30 Claims, 1 Drawing Sheet

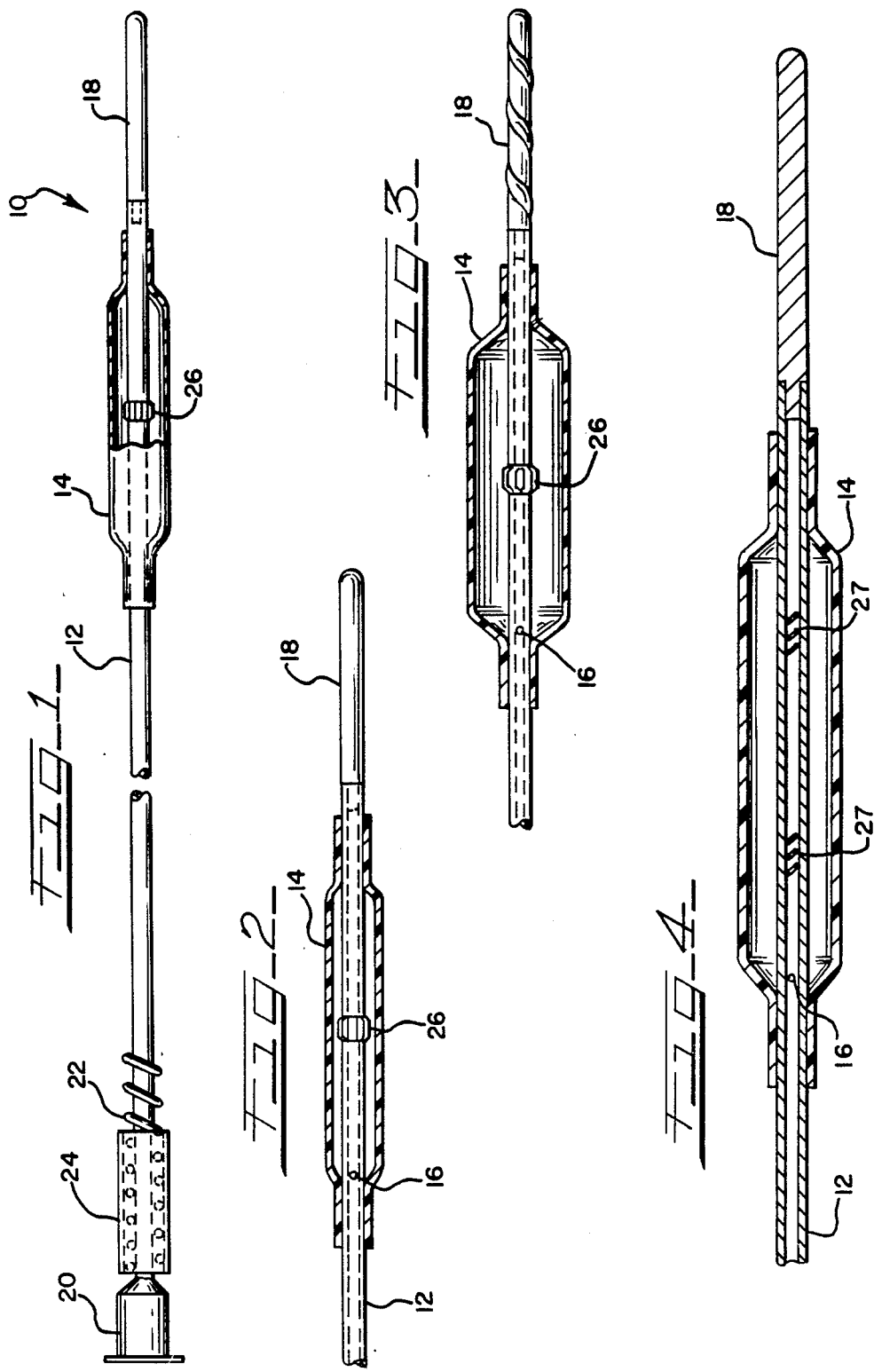

TRANSLUMINAL ANGIOPLASTY APPARATUS

BACKGROUND AND SUMMARY OF THE INVENTION

The present invention relates to surgical devices. More specifically, the invention relates to devices for performing transluminal angioplasty utilizing an expandable balloon member mounted on and affixed to a hollow guidewire. The balloon may be inflated by introducing a fluid or a gas through the guidewire and into the expandable balloon member to thereby dilate a lesion within a blood vessel.

Devices for performing transluminal angioplasty are known in the art. Such devices are used in procedures by which obstructions in blood vessels are altered in order to increase blood flow through the obstructed area of the vessel. Typically, a partially occluded blood vessel is enlarged by use of a balloon catheter that is passed percutaneously through the arterial system until the balloon member is properly positioned at the site of the occlusion or lesion. The properly positioned balloon member is then inflated to dilate the lumen of the blood vessel at the site of occlusion. Balloon catheters typically include thin flexible lengths of tubing having a small inflatable balloon mounted at or near the distal end of the tubing. The catheters are designed to be inserted and positioned within the lumen of a blood vessel, typically with fluoroscopic guidance and by use of a guidewire for improving the pushability or trackability of the otherwise flexible tubing.

The utility of prior art angioplasty catheters has typically been limited, in one aspect, by the available dimensions of the synthetic tubing relative to the internal diameter of the vessel requiring treatment. This limitation is especially significant where the catheter includes inner and outer catheter tubes to allow for the sampling and further treatment of the patient's blood during performance of the angioplasty procedure. Further, the need for and the use of a solid metallic guidewire to improve the pushability or trackability of the otherwise flexible synthetic catheter has necessarily required a cross-sectional catheter diameter greater than that of the guidewire. Such dimensional limitations have prevented prior art angioplasty catheters from being used in certain narrow blood vessels.

The present invention provides an apparatus for performing transluminal angioplasty which may be utilized in blood vessels of very small cross-sectional diameter as well as in blood vessels of larger diameter. In its preferred embodiment, the apparatus of the present invention includes a hollow stainless steel guidewire with an expandable balloon member affixed to the hollow guidewire at or near the distal end thereof.

The use of stainless steel, or another suitable metallic material, provides a catheter having an extremely small outer diameter while imparting good torque control and excellent pushability. The stainless steel guidewire is radiopaque to facilitate viewing of the catheter by use of a fluoroscope when the catheter is passed percutaneously through the arterial system. A high degree of torque control allows the stainless steel catheter to be vibrated or even rotated to aid in the insertion of the catheter and in the emulsification of blood clots within the treated blood vessel.

It is accordingly an object of the present invention to provide an apparatus for performing transluminal angioplasty.

It is another object of the present invention to provide an apparatus for performing transluminal angioplasty which utilizes a catheter having an extremely small cross-sectional diameter.

It is still another object of the present invention to provide an apparatus for performing transluminal angioplasty wherein the apparatus includes a catheter which provides good torque control during the insertion of the apparatus within the arterial system.

It is still another object of the present invention to provide an apparatus for performing transluminal angioplasty which has excellent pushability or trackability.

BRIEF DESCRIPTION OF THE DRAWINGS

These and other objects of the present invention will be more fully appreciated by those skilled in the art upon consideration of the remainder of the disclosure, including the drawings of which:

FIG. 1 is an elevational view, partially in section, of an apparatus for performing transluminal angioplasty in accordance with the present invention;

FIG. 2 is a side elevational view, partially in section, of the distal portion of the apparatus of FIG. 1 with the balloon member in a deflated state;

FIG. 3 is a side elevational view, partially in section, of an alternate embodiment for the distal portion of the apparatus of FIG. 1 and showing the balloon member in an inflated state; and FIG. 4 is an enlarged cross-sectional view, with slight modification, of the distal portion of the apparatus of FIG. 3.

DETAILED DESCRIPTION OF THE INVENTION

Referring generally to FIGS. 1 through 4, an apparatus 10 for performing transluminal angioplasty is illustrated. The apparatus 10 includes a metallic hollow guidewire 12 which is preferably made of stainless steel and has a very small outer diameter. Typically, the guidewire of the present invention will have an outer diameter of less than about 0.04 inches More specifically, the preferred metallic hollow guidewire of the present invention will have an outer diameter of about 0.014 inches to facilitate insertion of the device 10 into very narrow blood vessels. An expandable balloon member 14 is affixed to the metallic hollow guidewire 12 at or near the distal end thereof. A fill hole 16 is provided in the wall of the hollow guidewire 12 along the section of guidewire enclosed within the expandable balloon member 14.

Preferably, the balloon member 14 is made of nylon which may be melt fused or adhesively affixed to the guidewire 12 with one or more adhesives or with a combination of heat and an adhesive to provide a good nylon to metal bonding. Suitable adhesives may include silicone rubber, epoxy, urethane adhesives, isocyanate terminated polymers, cyanoacrylates, and the like. Additionally, as known by those skilled in the art, the surface of the guidewire 12 or the balloon 14 may be primed and adhesively bonded to each other with various silanes such as aminosilanes, hydroxysilanes, isocyanate silanes, glycidilsilanes and the like.

The proximal end of the apparatus 10 includes a hub 20, a strain relief coil 22 slidably positioned on the guidewire 12, and a sleeve 24 which lies over the coil 22. The sleeve 24 and the coil 22 allow the guidewire 12 to be more easily handled during insertion by helping to prevent crimping of the guidewire 12 when flexed, bent, or rotated during the percutaneous insertion thereof.

The metallic guidewire is radiopaque. Consequently, the guidewire 12 may be viewed under a fluoroscope during insertion. Additional radiopaque means, such as crimped metallic band 26, are provided so that the portion of the guidewire 12 which carries the expandable balloon member 14 can be fluoroscopically distinguished from the remainder of the apparatus 10. In this arrangement of parts, the crimped band 26 allows the surgeon, viewing the apparatus 10 under a fluoroscope, to distinguish between the portion of apparatus 10 carrying the balloon member 14 and the rest of the guidewire to thereby facilitate proper positioning of the balloon member 14 at the occluded area of the blood vessel.

Referring generally to FIGS. 2 and 3, the balloon member 14 is inserted within a blood vessel in a deflated state (FIG. 2) to thereby facilitate the percutaneous travel of the apparatus 10 to the occluded site within the vessel. Drugs, such as heparin, can be incorporated on the balloon/catheter wall to prevent blood clotting during use within the blood vessel. Lubricious agents such a Teflon, hydrogels, and the like may be used to ease insertion of the apparatus 10 into the vessel. Under fluoroscopic examination, the surgeon is able to monitor the travel of the apparatus 10 within the blood vessel. As mentioned, the presence of radiopaque means allows the surgeon to properly position the balloon member 14 within the occlusion or lesion. For example, the crimped metallic band 26 is preferably mounted at the centermost portion of the guidewire 12 within the balloon member 14. Therefore, positioning of the guidewire 12 such that the band 26 is positioned in the center of the occluded site will simultaneously position the balloon member 14 so that the center of the balloon member is also positioned within the center of the occlusion or lesion.

As known by those skilled in the art, the radiopaque means may include tungsten, lead, or the like. As an alternative to the crimped band 26, the radiopaque means may include a tungsten coiled wire 27 (as shown in FIG. 4), a solid tungsten wire, or other suitable material affixed within the lumen or inner surface of the guidewire 12, for example.

Distal end means 18 are provided to seal the distal end of the metallic hollow guidewire 12. The end means 18 can include a solid or coiled guidewire, a polymeric material or combinations thereof which may be threaded (FIG. 3) to facilitate insertion of the apparatus 10 through a stubborn lesion, such as by rotation of the apparatus so that the threaded distal end means function to effectively "drill" its way through the stubborn lesion. Additionally, in cases where the percutaneous travel of the apparatus 10 will require bending and turning during its travel within the vessel, it is desirable that the distal ends means 18 include no sharp edges. Preferably, especially where polymeric materials are used, the distal end means will include a rounded or spherical tip thereon so that the apparatus 10 can be vibrated or rotated to facilitate bending around a turn in the vessel while simultaneously avoiding injury to the lumen wall of the blood vessel. Further, the guidewire 12 may be drawn through a die to reduce its diameter, thereby increasing its flexibility without altering its tubular construction. It should be noted that elaborate distal end means are not necessary to the uses of the present invention. Therefore, the guidewire 12 can also be sealed at its distal end by the use of an epoxy or solder and the like.

Once the balloon member 14 has been properly positioned at the site of an occlusion or lesion, radiopaque fluid, such as renographin, can be injected through the guidewire 12 and into the balloon member 14 through the fill hole 16. In this manner, the balloon member 14 is expanded for treatment of the occlusion or lesion. The apparatus 12 may include one or more fill holes 16 which have been drilled or otherwise formed in the wall of the guidewire 12. Suitable means for placement of the fill holes 16 included laser drilling, electrical discharge machining, and the like.

After performing the transluminal angioplasty, the balloon member 14 may be deflated by allowing the fluid or gas within the balloon to pass back through the fill hole 16 and through the hollow guidewire 12. Once the balloon member 14 has been deflated to an appropriate extent, the apparatus 10 may be withdrawn from the blood vessel in a conventional manner.

While the preferred embodiment of the present invention has been discussed and described above, it will be understood that various changes and modifications can be made by those skilled in the art without departing from the true spirit and scope of the invention as defined in the following claims.

What is claimed is:

1. A surgical apparatus for performing transluminal angioplasty, comprising:
    a hollow metallic guidewire having a proximal end and a distal end;
    an expandable balloon member affixed to said hollow guidewire near said distal end; and
    a fill hole located in the wall of said hollow guidewire and within said expandable balloon member when said balloon member is affixed to said guidewire.

2. The surgical apparatus of claim 1, wherein said hollow metallic guidewire further includes distal end means for sealing said distal end of said guidewire.

3. The surgical apparatus of claim 1, wherein said hollow metallic guidewire is made of stainless steel.

4. The surgical apparatus of claim 1, wherein said hollow metallic guidewire has an outer diameter less than about 0.04 inches.

5. The surgical apparatus of claim 4, wherein said hollow metallic guidewire has an outer diameter of about 0.014 inches.

6. The surgical apparatus of claim 1, wherein said expandable balloon member is adhesively affixed to said hollow guidewire with one or more substances selected from the group consisting essentially of silicone rubber adhesives, epoxy adhesives, urethane adhesives, isocyanate terminated polymers, cyanoacrylates, aminosilanes, hydroxysilanes, isocyanatesilanes, and glycidilsilanes.

7. The surgical apparatus of claim 6, wherein said expandable balloon member is affixed to said guidewire with one or more of said substances and with the application of heat.

8. The surgical apparatus of claim 1, wherein said balloon member is melt fused to said guidewire.

9. The surgical apparatus of claim 1, wherein said expandable balloon member is inflated by the passage of fluid from within said hollow guidewire through said fill hole and into said expandable balloon.

10. The surgical apparatus of claim 1, wherein said expandable balloon member is made from nylon.

11. The surgical apparatus of claim 2, wherein said distal end means is a solid metallic guidewire.

12. The surgical apparatus of claim 2, wherein said distal end means is a polymeric material.

13. The surgical apparatus of claim 2, wherein the outer surface of said distal end means is threaded.

14. The surgical apparatus of claim 1, further comprising radiopaque means affixed to said guidewire and within said expandable balloon member for positioning said balloon member within a blood vessel under fluoroscopic examination thereof, said radiopaque means being a metallic material for providing contrast with said guidewire when viewed under said fluoroscope.

15. The surgical apparatus of claim 14, wherein said radiopaque means is affixed around the outer surface of said guidewire.

16. The surgical apparatus of claim 14, wherein said radiopaque means is affixed to the inner surface of said guidewire.

17. A surgical apparatus for performing transluminal angioplasty, comprising:
a stainless steel hollow guidewire having a proximal end and a distal end, said hollow guidewire having an outer diameter of less than about 0.04 inches;
an expandable balloon member affixed to said hollow guidewire near said distal end; and
a fill hole located in the side of said hollow guidewire and within said expandable balloon member when said balloon member is affixed to said guidewire.

18. The surgical apparatus of claim 17, wherein said hollow guidewire further includes distal end means for sealing said distal end of said guidewire.

19. The surgical apparatus of claim 17, wherein said hollow metallic guidewire has an outer diameter of about 0.014 inches.

20. The surgical device of claim 17, wherein said expandable balloon member is adhesively affixed to said hollow guidewire with one or more substances selected from the group consisting essentially of silicone rubber adhesives, epoxy adhesives, urethane adhesives, isocyanate terminated polymers, cyanoacrylates, aminosilanes, hydroxysilanes, isocyanatesilanes, glycidilsilanes 21. The surgical device of claim 20, wherein said expandable balloon member is affixed to said guidewire with one or more of said substances and with the application of heat.

22. The surgical device of claim 17, wherein said balloon member is melt fused to said guidewire.

23. The surgical apparatus of claim 17, wherein said expandable balloon member is inflated by the passage of liquid from within said hollow guidewire through said fill hole and into said expandable balloon.

24. The surgical apparatus of claim 17, wherein said expandable balloon member is made from nylon.

25. The surgical apparatus of claim 18, wherein said distal end means is a solid metallic guidewire.

26. The surgical apparatus of claim 18, wherein said distal end means is a polymeric material.

27. The surgical apparatus of claim 18, wherein the outer surface of said distal end means is threaded.

28. The surgical apparatus of claim 17, further comprising radiopaque means affixed to said guidewire and within said expandable balloon member for positioning said balloon member within a blood vessel under fluoroscopic examination thereof, said radiopaque means being a metallic material for providing contrast with said guidewire when viewed under said fluoroscope.

29. The surgical apparatus of claim 28, wherein said radiopaque means is affixed around the outer surface of said guidewire.

30. The surgical apparatus of claim 28, wherein said radiopaque means is affixed to the inner surface of said guidewire.

* * * * *